United States Patent
Kase et al.

(10) Patent No.: US 8,419,630 B2
(45) Date of Patent: Apr. 16, 2013

(54) ENDOSCOPE SYSTEM WITH FRONT AND LATERAL FIELDS OF VIEW

(75) Inventors: Seigo Kase, Hino (JP); Yasuhito Kura, Hachioji (JP); Yuji Sakamoto, Kunitachi (JP)

(73) Assignee: Olympus Medical Systems Corp., Tokyo (JP)

(*) Notice: Subject to any disclaimer, the term of this patent is extended or adjusted under 35 U.S.C. 154(b) by 171 days.

(21) Appl. No.: 13/036,581

(22) Filed: Feb. 28, 2011

(65) Prior Publication Data

US 2011/0275889 A1 Nov. 10, 2011

Related U.S. Application Data

(63) Continuation of application No. PCT/JP2010/067951, filed on Oct. 13, 2010.

(30) Foreign Application Priority Data

Nov. 6, 2009 (JP) ................................ 2009-255186

(51) Int. Cl.
*A61B 1/04* (2006.01)
(52) U.S. Cl.
USPC ........................... 600/170; 600/168; 600/118
(58) Field of Classification Search .................. 600/109, 600/118, 168, 170, 171, 176; 348/84, 85; 345/634, 635
See application file for complete search history.

(56) References Cited

U.S. PATENT DOCUMENTS

| | | | |
|---|---|---|---|
| 5,710,661 A * | 1/1998 | Cook ............................. | 359/364 |
| 7,110,124 B2 * | 9/2006 | Jensen et al. .................. | 356/626 |
| 7,408,703 B2 * | 8/2008 | Matsuki et al. ............... | 359/365 |
| 7,922,655 B2 * | 4/2011 | Yasushi et al. ................ | 600/173 |
| 2001/0055062 A1 | 12/2001 | Shioda et al. | |
| 2004/0220478 A1 * | 11/2004 | Wallace et al. ............... | 600/476 |
| 2004/0254424 A1 * | 12/2004 | Simkulet et al. ............. | 600/176 |
| 2005/0010082 A1 | 1/2005 | Nishimura et al. | |
| 2008/0009714 A1 | 1/2008 | Oda | |
| 2008/0045797 A1 * | 2/2008 | Yasushi et al. ............... | 600/175 |
| 2009/0041320 A1 | 2/2009 | Tanaka | |

(Continued)

FOREIGN PATENT DOCUMENTS

| EP | 1 437 083 A1 | 7/2004 |
|---|---|---|
| EP | 1 867 271 A1 | 12/2007 |

(Continued)

*Primary Examiner* — John P Leubecker
(74) *Attorney, Agent, or Firm* — Scully Scott Murphy & Presser, PC

(57) ABSTRACT

An endoscope system including an endoscope which acquires a front field-of-view image and a lateral field-of-view image of an object of observation; a detecting section which has a function capable of detecting whether a treatment instrument is used or not in the endoscope based on a notification signal which is outputted when the treatment instrument is inserted into the endoscope; and an image processing section. The image processing section generates an observation image including the front field-of-view image and the lateral field-of-view image within the same screen, displays a magnified image of one field-of-view image out of the front field-of-view image and the lateral field-of-view image on a display, and performs adjacent part display processing of displaying only a part of the one field-of-view image which is adjacent to the other field-of-view image or image compression processing of displaying a compressed image of the other field-of-view image on the display.

16 Claims, 11 Drawing Sheets

U.S. PATENT DOCUMENTS

| | | | |
|---|---|---|---|
| 2009/0112061 A1* | 4/2009 | Kim et al. | 600/109 |
| 2009/0198104 A1 | 8/2009 | Sugiyama | |
| 2011/0196200 A1* | 8/2011 | Glozman et al. | 600/109 |
| 2012/0065468 A1* | 3/2012 | Levy et al. | 600/109 |

FOREIGN PATENT DOCUMENTS

| | | |
|---|---|---|
| EP | 2 008 571 A1 | 12/2008 |
| EP | 2 082 678 A1 | 7/2009 |
| EP | 2 085 017 A1 | 8/2009 |
| JP | 05-049599 | 3/1993 |
| JP | 5-28302 | 4/1993 |
| JP | 05-297288 | 11/1993 |
| JP | 06-030335 | 2/1994 |
| JP | 06-181885 | 7/1994 |
| JP | 09-149876 | 6/1997 |
| JP | 09-313435 | 12/1997 |
| JP | 11-032982 | 2/1999 |
| JP | 2000-116598 | 4/2000 |
| JP | 2002-014287 | 1/2002 |
| JP | 2003-093328 | 4/2003 |
| JP | 2004-041778 | 2/2004 |
| JP | 2006-235346 A | 9/2006 |
| JP | 2007-282857 | 11/2007 |
| JP | 2007-330348 | 12/2007 |
| JP | 2008-136628 | 6/2008 |
| JP | 2008-154758 | 7/2008 |
| JP | 2008-309860 | 12/2008 |
| JP | 2009-045358 A | 3/2009 |
| JP | 2009-178416 | 8/2009 |
| JP | 2010117665 A * | 5/2010 |
| WO | 2008/065955 A1 | 6/2008 |

* cited by examiner

LATERAL FIELD-OF-VIEW IMAGE  FRONT FIELD-OF-VIEW IMAGE

LATERAL FIELD-OF-VIEW IMAGE    FRONT FIELD-OF-VIEW IMAGE

LATERAL FIELD-OF-VIEW IMAGE    FRONT FIELD-OF-VIEW IMAGE

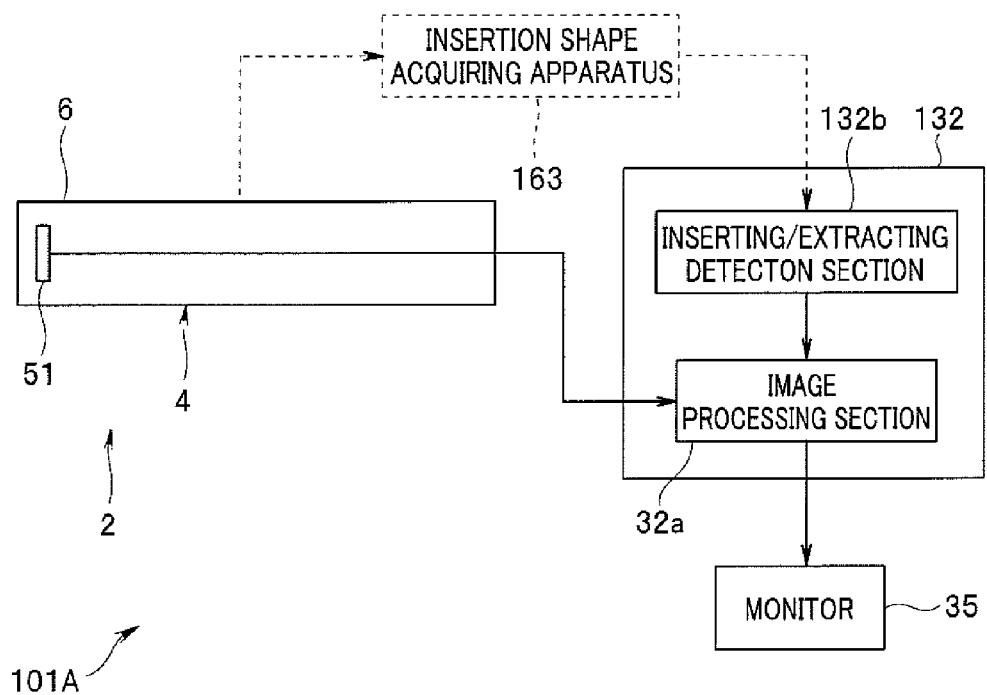
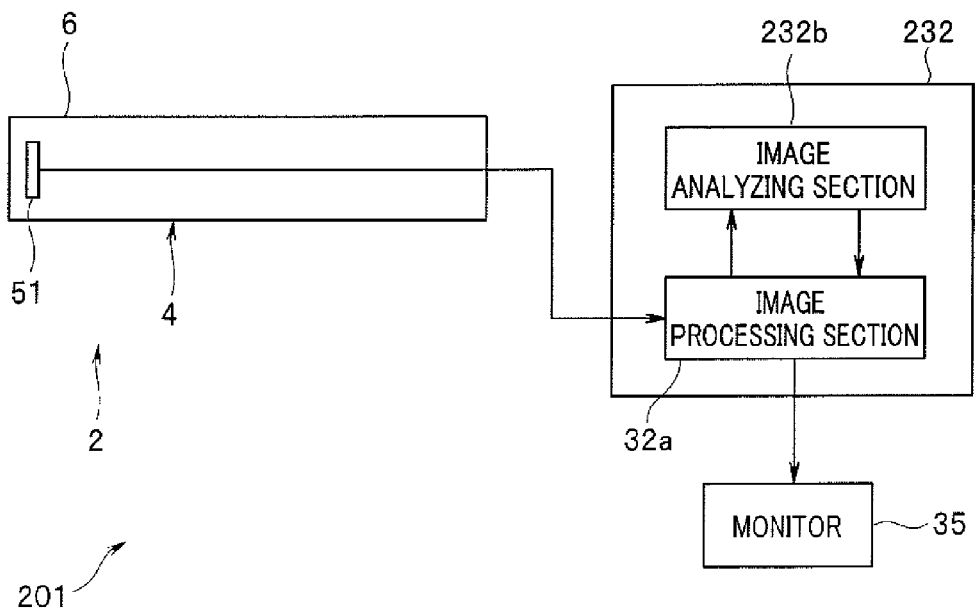

LATERAL FIELD-OF-VIEW IMAGE
(PARTIAL DISPLAY OR COMPRESSED DISPLAY)

FRONT FIELD-OF-VIEW IMAGE
(MAGNIFIED DISPLAY)

LATERAL FIELD-OF-VIEW IMAGE
(MAGNIFIED DISPLAY)

FRONT FIELD-OF-VIEW IMAGE
(PARTIAL DISPLAY OR COMPRESSED DISPLAY)

LATERAL FIELD-OF-VIEW IMAGE    FRONT FIELD-OF-VIEW IMAGE

LATERAL FIELD-OF-VIEW IMAGE    FRONT FIELD-OF-VIEW IMAGE

LATERAL FIELD-OF-VIEW IMAGE    FRONT FIELD-OF-VIEW IMAGE

LATERAL FIELD-OF-VIEW IMAGE    FRONT FIELD-OF-VIEW IMAGE

DARK PART

ENDOSCOPE SYSTEM WITH FRONT AND LATERAL FIELDS OF VIEW

CROSS REFERENCE TO RELATED APPLICATION

This application is a continuation application of PCT/JP2010/067951 filed on Oct. 13, 2010 and claims benefit of Japanese Application No. 2009-255186 filed in Japan on Nov. 6, 2009, the entire contents of which are incorporated herein by this reference.

BACKGROUND OF THE INVENTION

1. Field of the Invention

The present invention relates to an endoscope system and in particular to an endoscope system capable of making observations in a front-viewing direction and also in a lateral-viewing direction simultaneously.

2. Description of the Related Art

An endoscope system which comprises an endoscope for picking up an image of an object interior of a subject to be examined, an image processing apparatus for generating an observation image of the object picked up by the endoscope and so forth has been widely used in a medical field and an industrial field.

For example, Japanese Patent Laid-Open Publication No. 2008-309860 discloses an optical system capable of simultaneously acquiring an image of an object in a front-viewing direction which corresponds to a central axis direction and an image of an object in every direction of a lateral-viewing direction, which is substantially perpendicular to the central axis direction, and an endoscope equipped with the optical system. And then, according to the endoscope equipped with the optical system as disclosed in Japanese Patent Laid-Open Publication No. 2008-309860, an image in a round shape in the front-viewing direction (a front field-of-view image) and an entire circumferential image in the lateral-viewing direction (a lateral field-of-view image) having a circular ring shape on an outer circumference of the image in the front-viewing direction (a lateral field-of-view image) are displayed on a display unit such as a monitor.

SUMMARY OF THE INVENTION

An endoscope system of the present invention comprises: an endoscope which acquires a front field-of-view image and a lateral field-of-view image of an object of observation; a detecting section which has a function capable of detecting whether a treatment instrument is used or not in the endoscope based on a notification signal which is outputted when the treatment instrument is inserted into the endoscope; and an image processing section which generates an observation image including the front field-of-view image and the lateral field-of-view image within the same screen, displays a magnified image of one field-of-view image out of the front field-of-view image and the lateral field-of-view image on a display section, and performs adjacent part display processing of displaying only a part of the one field-of-view image which is adjacent to the other field-of-view image or image compression processing of displaying a compressed image of the other field-of-view image on the display section.

BRIEF DESCRIPTION OF THE DRAWINGS

FIG. 10 is a diagram showing a configuration of a main part in a modified example of the second embodiment;

FIG. 11 is a diagram showing a configuration of a main part in a third embodiment;

DETAILED DESCRIPTION OF THE PREFERRED EMBODIMENTS

Figure 1:
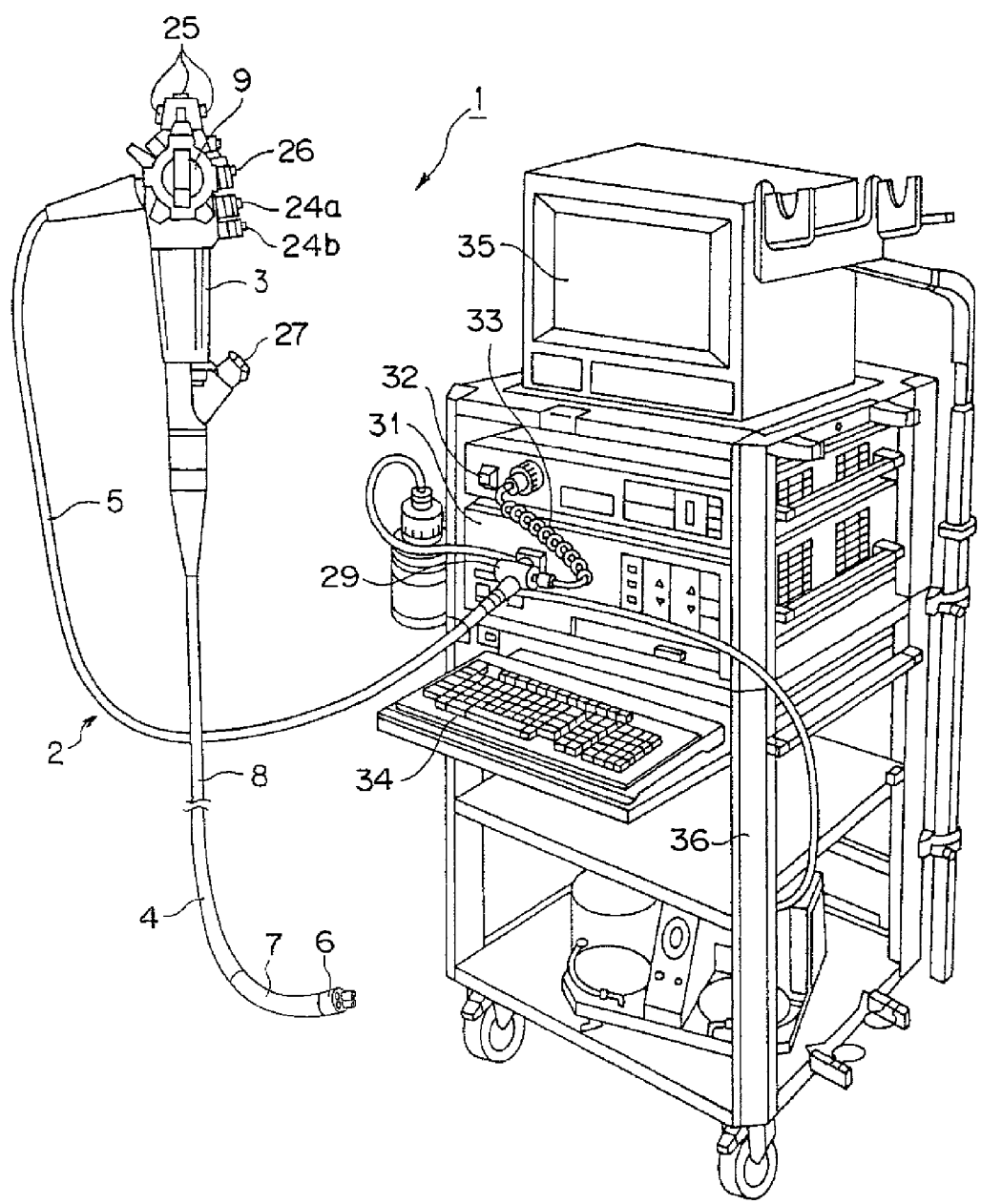
FIG. 1 is a view showing a configuration of an endoscope system according to an embodiment of the present invention.

Hereinafter, embodiments of the present invention will be described referring to the drawings.

First Embodiment

As shown in FIG. 1, an endoscope system 1 comprises an endoscope 2 which picks up an image of an object of observation and outputs an image pickup signal, a light source apparatus 31 for supplying illumination light for illuminating the object of observation, a video processor 32 which generates and outputs a video signal according to the image pickup signal and a motor 35 for displaying an observation image according to the video signal.

The endoscope 2 is configured to include an operation portion 3 to be grasped by an operator for performing an operation, an elongated insertion portion 4 which is formed on a distal end side of the operation portion 3, to be inserted into a body cavity and the like, and a universal cord 5 having one end which is provided such that the cord extends from a side portion of the operation portion 3.

The insertion portion 4 is configured to include a hard distal end portion 6, a bendable bending portion 7 provided at a rear end of the distal end portion 6, a long flexible tube portion 8 having flexibility and provided at a rear end of the bending portion 7. It is noted that the bending portion 7 performs a bending action in accordance with an operation on a bending operation lever 9 provided at the operation portion 3.

Figure 2:
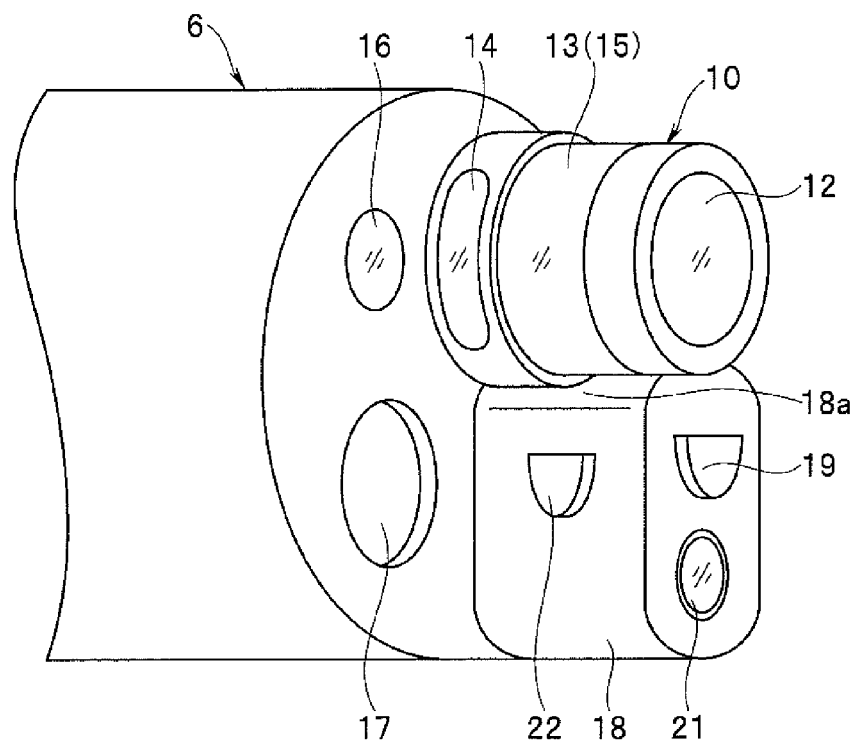
FIG. 2 is a perspective view showing a configuration of a distal end portion of an insertion portion of the endoscope.

On the other hand, as shown in FIG. 2, on the distal end portion 6 of the insertion portion 4, a cylindrical portion 10 in a cylinder shape is formed to be provided to protrude from a distal end face of the distal end portion 6 at a position eccentric upward from a center of the distal end face.

In a distal end portion of the cylindrical portion 10, there is provided an objective optical system, not shown, to be used for front viewing and lateral viewing. A distal end portion of the cylindrical portion 10 is configured to include a front-viewing observation window 12 which is arranged at a place corresponding to the front-viewing direction of the not-shown objective optical system, and a lateral-viewing observation window 13 arranged at a place corresponding to the lateral-viewing direction of the not-shown objective optical system. Further, in the vicinity of a proximal end of the cylindrical portion 10, a lateral-viewing illumination portion 14 is formed to emit light for illumination in the lateral-viewing direction.

The lateral-viewing observation window 13 comprises a lateral-viewing mirror lens 15 which enables to acquire a lateral field-of-view image by capturing return light (reflected light) from an object of observation inputted from a circumference of the cylindrical portion 10 having the cylinder shape within a lateral field-of-view.

In addition, at an imaging position of the not-shown objective optical system, (an image pickup surface of) an image pickup device is arranged such that an image of the object of observation within the field-of-view of the front-viewing observation window 12 is formed at a central part as a round front field-of-view image, and an image of the object of observation within the field-of-view of the lateral-viewing observation window 13 is formed on an outer circumferential side of the round front field-of-view image as a lateral field-of-view image in the shape of a circular ring.

On the distal end face of the distal end portion 6, there are provided a front-viewing illumination window 16 which is arranged at a position adjacent to the cylindrical portion 10 and emits illumination light in a range of the front field-of-view of the front-viewing observation window 12, and a distal end opening 17 which communicates with a treatment instrument channel, not shown, which is formed of a tube and the like disposed in the insertion portion 4 and is capable of projecting (a distal end of) a treatment instrument inserted into the treatment instrument channel.

Further, the distal end portion 6 of the insertion portion 4 has a support portion 18 provided to protrude from the distal end face of the distal end portion 6 and the support portion 18 is positioned to be adjacent to a lower side of the cylindrical portion 10.

The support portion 18 is configured to be capable of supporting (or holding) each of protruding portions which are arranged to protrude from the distal end face of the distal end portion 6. Specifically, the support portion 18 is configured to be capable of supporting (or holding) a nozzle portion 19 for the front-viewing observation window which injects gas or fluid for cleaning the front-viewing observation window 12, a front-viewing illumination window 21 which emits light for illumination in the front-viewing direction, and nozzle portions 22 for the lateral-viewing observation window which inject gas or liquid for cleaning the lateral-viewing observation window 13, as the aforesaid respective protruding portions.

On the other hand, the support portion 18 is formed to include a shielding portion 18a as an optical shielding member to prevent capturing of a lateral field-of-view image including any of the aforesaid protruding portions which are objects different from a target object of observation, due to presence of the aforesaid protruding portions within the lateral field-of-view. That is, it is possible to acquire a lateral field-of-view image excluding any of the nozzle portion 19 for front-viewing observation window, the front-viewing illumination window 21, and the nozzle portions 22 for lateral-viewing observation window by providing the support portion 18 with the shielding portion 18a.

Figure 3:
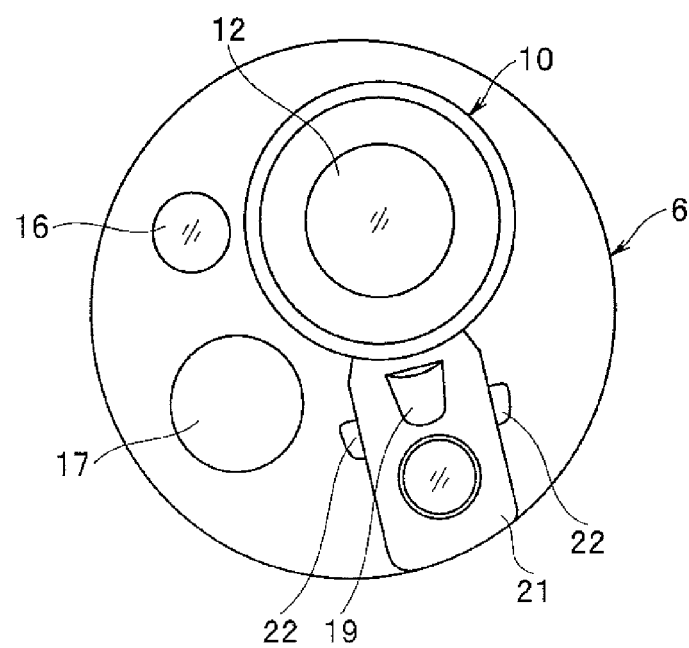
FIG. 3 is a front view showing the configuration of the distal end portion of the insertion portion of the endoscope.

As shown in FIG. 2 and FIG. 3, the nozzle portions 22 for lateral-viewing observation window are provided in two places on the support portion 18 and arranged such that distal ends of the nozzles respectively protrude from side faces of the support portion 18.

In the operation portion 3, there are provided a gas/liquid feeding operation button 24a which allows an instruction operation to inject gas or liquid for cleaning the front-viewing observation window 12 from the nozzle portion 19 for front-viewing observation window and a gas/liquid feeding operation button 24b which allows an instruction operation to inject gas or liquid for cleaning the lateral-viewing observation window 13 from the nozzle portions 22 for lateral-viewing observation window, and switching between a gas feed and a liquid feed can be performed by pressing the gas/liquid feeding operation buttons 24a and 24b. Further, in this embodiment, a plurality of gas/liquid feeding operation buttons are provided to respectively correspond to the nozzle portions, but it may be configured, for example, such that gas or liquid is injected from the nozzle portion 19 for front-viewing observation window and also the nozzle portions 22 for lateral-viewing observation window by an operation of one gas/liquid feeding operation button.

A plurality of scope switches 25 are provided at a top portion of the operation portion 3 and have configurations such that functions of the respective scope switches can be assigned to output signals which correspond to ON or OFF and so forth of various functions available in the endoscope 2. Specifically, for example, signals corresponding to functions of a start and a stop of a forward water feed, an execution and a cancellation of a freeze, and a notification of a using state of the treatment instrument can be assigned to the scope switches 25 as the functions of the respective switches.

In addition, in this embodiment, the function of at least one of the gas/liquid feeding operation buttons 24a and 24b may be assigned to any of the scope switches 25.

Further, on the operation portion 3, a suction operation button 26 is disposed to allow to issue an instruction for aspirating and collecting mucus and the like in a body cavity from the distal end opening 17, to a suction unit and the like, not shown.

Then, the mucus and the like in the body cavity sucked according to an operation of the not-shown aspiration unit are corrected in a suction bottle and the like of the not-shown suction unit through the distal end opening 17, a treatment instrument channel, not shown, in the insertion portion 4, and a treatment instrument insertion opening 27 provided in the vicinity of a front end of the operation portion 3.

The treatment instrument insertion opening 27 communicates with the not-shown treatment instrument channel in the insertion portion 4 and is formed as an opening into which a treatment instrument, not shown, can be inserted. That is, an operator can perform treatment using a treatment instrument by inserting the treatment instrument into the treatment instrument insertion opening 27 and projecting a distal end side of the treatment instrument from the distal end opening 17.

On the other hand, as shown in FIG. 1, a connector 29 connectable to the light source apparatus 31 is provided at the other end of the universal cord 5.

A mouthpiece (not shown) serving as a connection end of a fluid conduit and a light guide mouthpiece (not shown) serving as a supply end of illumination light are provided at a distal end of the connector 29. Further, an electric contact portion (not shown) connectable with one end of a connection cable 33 is provided at a side surface of the connector 29. Furthermore, a connector for electrically connecting the endoscope 2 with the video processor 32 is provided at the other end of the connection cable 33.

A plurality of signal lines for transmitting various electric signals and a light guide for transmitting illumination light supplied from the light source apparatus 31 are built in the universal cord 5 in a bundled state.

The light guide built in from the insertion portion 4 through the universal cord 5 has a configuration such that an end portion on a light emitting side is split into at least two directions in the vicinity of the insertion portion 4, a light emitting end face of one split light guide is arranged at the front-viewing illumination windows 16 and 21, and a light emitting end face of the other split light guide is arranged at the lateral-viewing illumination portion 14. Further, the light guide has a configuration such that an end of the light guide on the light input side is arranged at the light guide mouthpiece of the connector 29.

Figure 4:
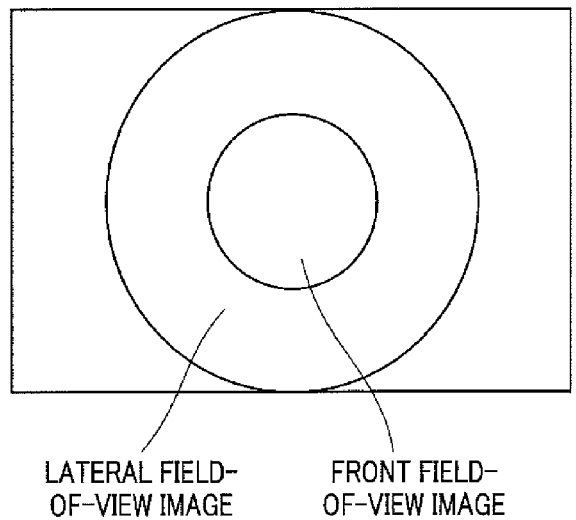
FIG. 4 is a diagram showing an example of an observation image displayed on a monitor.

The video processor 32 outputs a drive signal for driving the image pickup device provided in the distal end portion 6 of the endoscope 2. Then, the video processor 32 generates a video signal by performing signal processing with respect to an image pickup signal outputted from the image pickup device and outputs the video signal to the monitor 35. Thereby, an observation image comprising a front field-of-view image in a round shape and a lateral field-of-view image in a circular ring shape on an outer circumference of the image in the front-viewing direction is displayed on the monitor 35 in an appearance as shown in FIG. 4, for example. Besides, in observation images shown in this embodiment and the subsequent embodiments, it is assumed that a part of the image optically shielded by the shielding portion 18a of the support portion 18 is not taken into consideration. On the other hand, based on a signal outputted from one of the scope switches 25, the video processor 32 can detect that one function corresponding to the signal is turned on or off (in an operation detecting section 32b as described later).

Further, the video processor 32 performs image processing for changing a display appearance of the observation image which comprises the front field-of-view image and the lateral field-of-view image in the same screen, based on various factors as described in detail later.

Peripheral equipments such as the light source apparatus 31, the video processor 32 and the monitor 35 are arranged on a frame 36 with a keyboard 34 for performing an input of patient information, etc.

Next, an operation of the present embodiment will be described.

Figure 5:
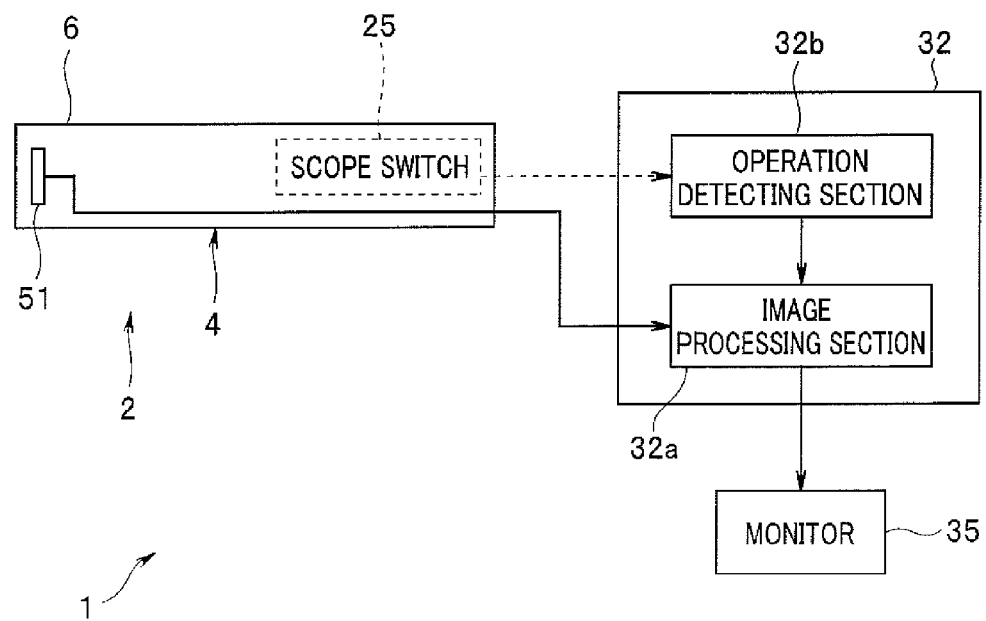
FIG. 5 is a diagram showing a configuration of a main part in a first embodiment.

First, in the endoscope system 1, the main part of which is shown in FIG. 5, respective components of the image pickup device 51 provided at the distal end portion 6 of the endoscope 2, the video processor 32 and the monitor 35 are started up and thereby an image pickup signal is outputted from the image pickup device 51.

An image processing section 32a of the video processor 32 (see FIG. 5) generates a video signal by performing signal processing with respect to an image pickup signal outputted from the image pickup device 51 and outputs the video signal to the monitor 35. Thereby, an observation image as shown in FIG. 4 is displayed on the monitor 35.

On the other hand, in order to perform a treatment using a desired treatment instrument, the operator inserts the desired treatment instrument into the treatment insertion opening 27 and projects a distal end of the desired treatment instrument from the distal end opening 17. In connection with this, the operator operates the scope switch 25 at any time during a period from the time of insertion of the desired treatment instrument into the treatment instrument insertion opening 27 till performance of an actual treatment after projecting the distal end of the desired treatment instrument from the distal end opening 17, to output a treatment instrument in use notifying signal for notifying the video processor 32 that the treatment using the desired treatment instrument is to be performed.

Besides, the treatment instrument in use notifying signal is not limited to a signal outputted in response to an operation of the scope switch 25, but may be one which is outputted as an output signal from an optical sensor provided in at least one of the vicinity of the distal end opening 17 and the vicinity of the treatment instrument insertion opening 27.

An operation detecting section 32b of the video processor 32 (see FIG. 5) detects that the treatment instrument is used in the endoscope 2 based on the treatment instrument in use notifying signal outputted from the scope switch 25 and outputs a detection result to the image processing section 32a.

When a detection result that the treatment instrument is used in the endoscope 2 is outputted from the operation detecting section 32b, the image processing section 32a performs processing of magnifying a front field-of-view image (enlarging a display size on the monitor) and performs image processing of changing a display appearance of a lateral field-of-view image in accordance with the magnification of the front field-of-view image.

Figure 15:
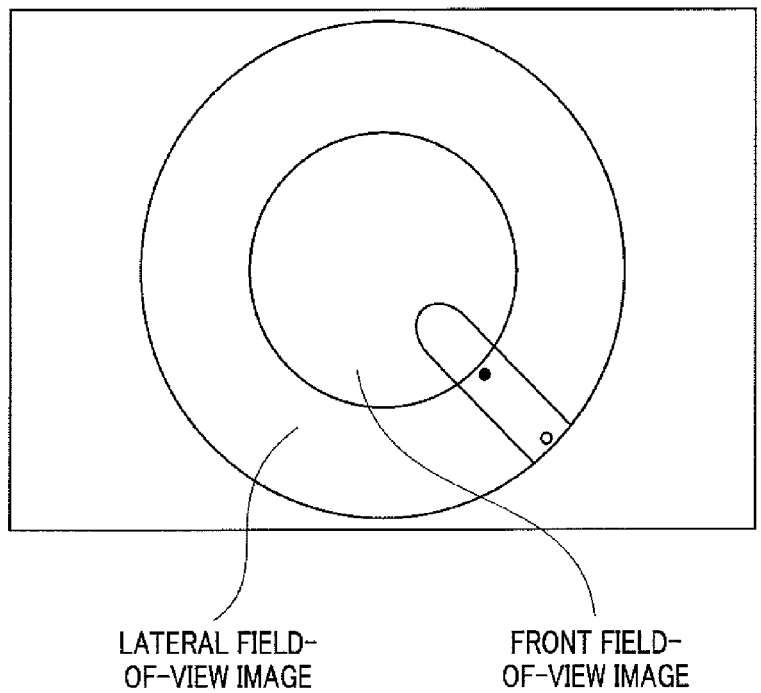
FIG. 15 is a diagram showing an example of an original image as an object of image processing.
Figure 16:
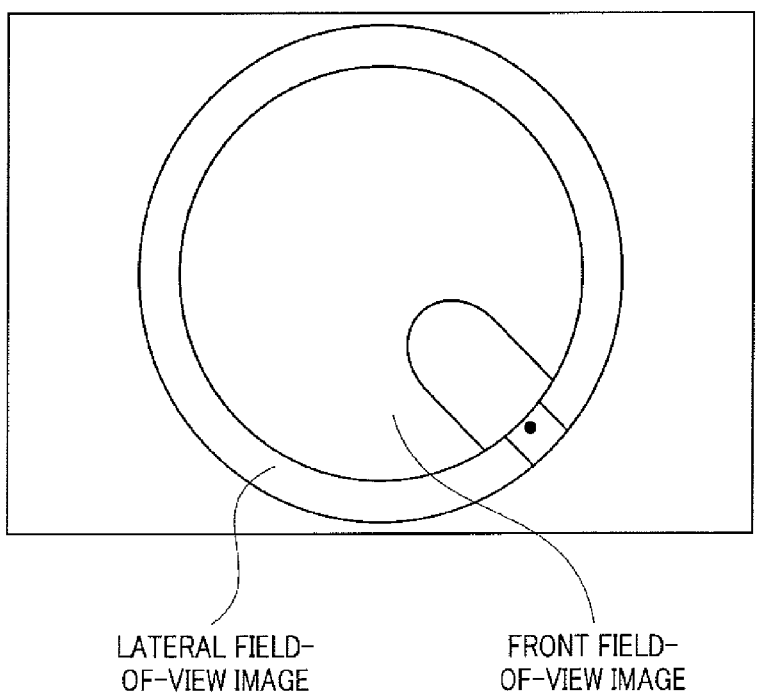
FIG. 16 is a diagram showing an example of a case where only a part of the original lateral field-of-view image of FIG. 15 in a range adjacent to the magnified front field-of-view image is displayed.
Figure 17:
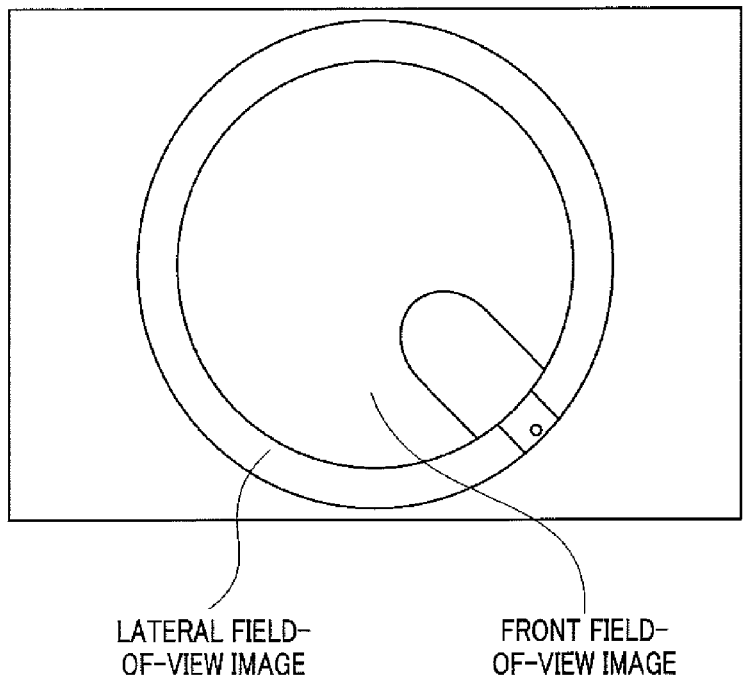
FIG. 17 is a diagram showing an example of a case where only a part of the original lateral field-of-view image of FIG. 15 in a range which is not covered by the magnified front field-of-view image.
Figure 18:
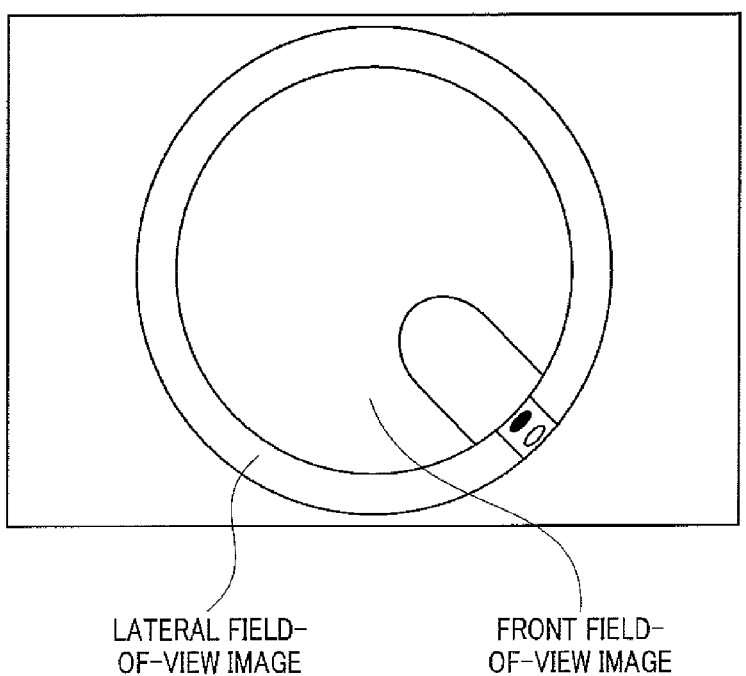
FIG. 18 is a diagram showing an example in a case where a compressed image obtained by image compression processing on the original lateral field-of-view image of FIG. 15 is displayed while maintaining a visual field range of the original lateral field-of-view image.

Specifically, the image processing of changing the display appearance of the lateral field-of-view image may be, for example, processing of displaying only a part (a central side of the original image) of the original lateral field-of-view image shown in FIG. 15 in a range adjacent to the magnified front field-of-view image on the monitor 35 (FIG. 16), and processing of displaying only a part (an outer peripheral side of the original image) of the original lateral field-of-view image in a range not covered by the magnified front field-of-view image on the monitor 35 (FIG. 17). Alternatively, the image processing of changing the display appearance of the lateral field-of-view image may be, for example, processing of displaying a compressed image obtained by performing image compression processing with respect to the original lateral field-of-view image while maintaining the field-of-view range of the original lateral field-of-view image on the monitor 35 (FIG. 18).

Figure 13:
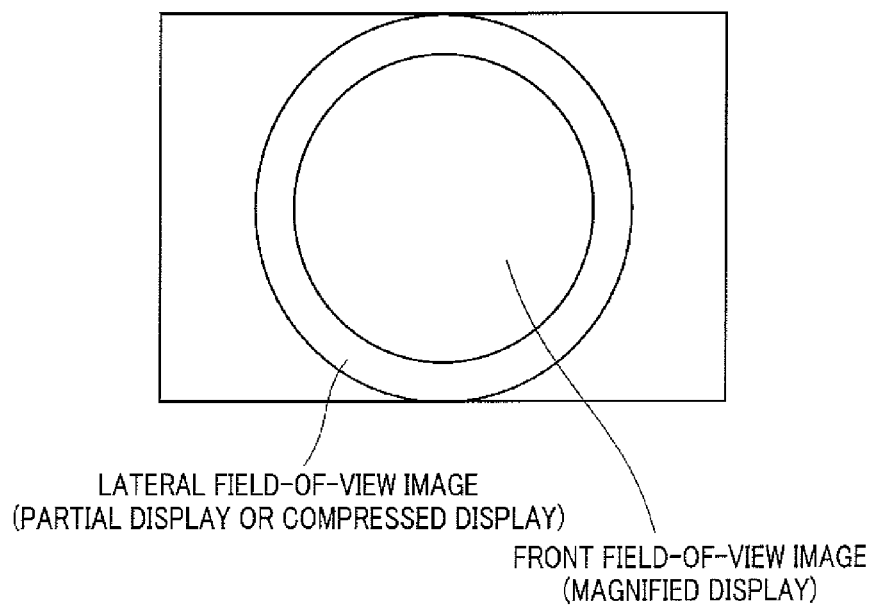
FIG. 13 is a diagram showing an example of a display appearance of the observation image of FIG. 4 in which a front field-of-view image is magnified.

Then, the image processing section 32a generates an observation image in a display appearance as shown in FIG. 13, for example, by performing the above-mentioned processing with respect to the front field-of-view image and the lateral field-of-view image, and outputs the observation image to the monitor 35. In the observation image exemplified in FIG. 13, an image which corresponds to a part of the original lateral field-of-view image or a compressed image of the original lateral field-of-view image is displayed with the magnified display of the front field-of-view image.

Here, when performing an endoscopy using a treatment instrument, it is common for an operator to use a technique of projecting the treatment instrument to face an affected part in the front-viewing direction. Thus, according to the observation image having the display appearance as shown in FIG. 13, the operator can smoothly perform a series of operations of projecting the treatment instrument in the front-viewing direction to approach the affected part while viewing the magnified front field-of-view image.

Besides, the present embodiment is not limited to the configuration in which the magnified front field-of-view image is displayed (the observation image in the display appearance as shown in FIG. 13) when performing the treatment using the treatment instrument, but may have a configuration in which the magnified front field-of-view image is displayed (the observation image in the display appearance as shown in FIG. 13) when a signal for instructing a start of a forward water feed is outputted from the scope switch 25.

As described above, according to the present embodiment, in the observation image allowing the observation in the front-viewing direction and also in the lateral-viewing direction simultaneously, visibility of the image in one of the viewing directions can be improved in accordance with at least one of the using state of the treatment instrument and the operation state of the scope switch.

Further, as a modified example of the present embodiment, it may be configured such that when a bending operation of the bending portion 7 is instructed by the bending operation lever 9, an observation image having a display appearance different from the aforementioned display appearances is generated and outputted.

Figure 6:
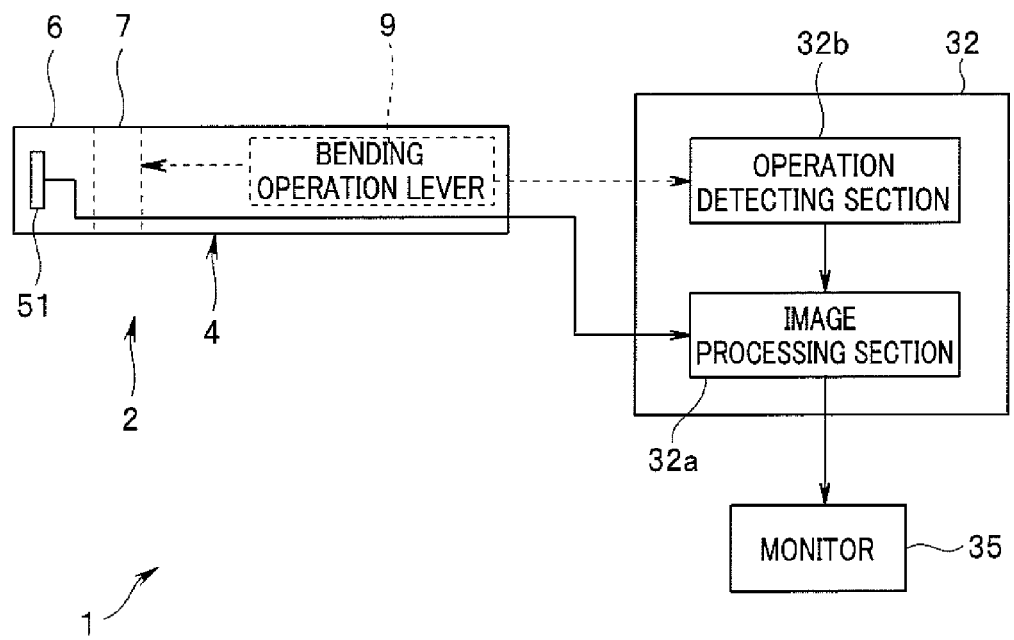
FIG. 6 is a diagram showing a configuration of a main part in a modified example of the first embodiment.

In such a case, as shown in FIG. 6, for example, the operation detecting section 32b of the video processor 32 detects a bending direction of the bending portion 7 based on an operation state of the bending operation lever 9 and outputs a detection result to the image processing section 32a.

When the detection result is outputted from the operation detecting section 32b, the image processing section 32a performs the image processing of transiting the display appearance of the observation image as exemplified by FIG. 4 to another display appearance corresponding to the bending direction.

As the image processing of transiting the display appearance of the observation image to another display appearance corresponding to the bending direction, it is possible to use first processing of enlarging a field-of-view range of the lateral field-of-view image corresponding to the bending direction and shifting the front field-of-view image in a direction opposite to the bending direction.

According to the aforesaid first processing, when it is detected that the bending portion 7 is bent upward, for example, the image processing section 32a enlarges an upward field-of-view range of the lateral field-of-view image and shifts the front field-of-view image downward. Thereby, the observation image displayed on the monitor 35 is transited from the image as shown in FIG. 4 to the image as shown in FIG. 7.

Figure 7:
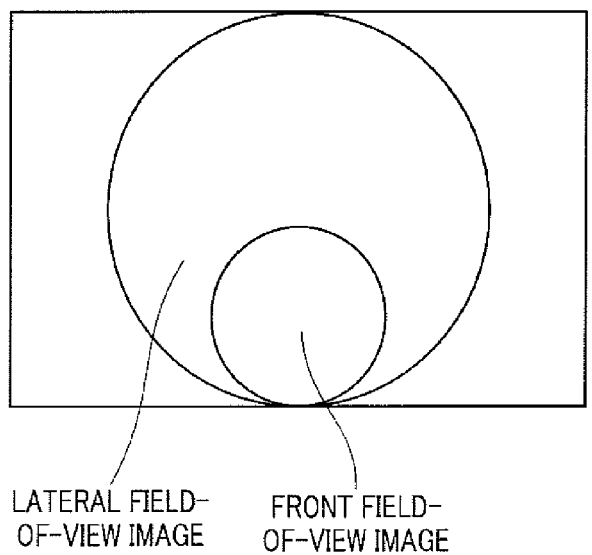
FIG. 7 is a diagram showing an example of a display appearance of an image after transition in the modified example of the first embodiment.

Besides, in the present embodiment, in the case where the observation image is transited from the image as shown in FIG. 4 to the image as shown in FIG. 7 by the first processing, a field-of-view range of the front field-of-view image is maintained. Further, the aforesaid first processing is applicable not only to a case where the bending portion 7 is bent upward but also to a case where the bending portion 7 is bent in a direction other than the upward direction in substantially the same manner.

On the other hand, as the image processing of transiting the display appearance of the observation image to another display appearance according to the bending direction of the bending portion 7, it is possible to use second processing of extracting a part of the observation image in the bending direction and magnifying the extracted part, instead of the aforesaid first processing.

Figure 8:
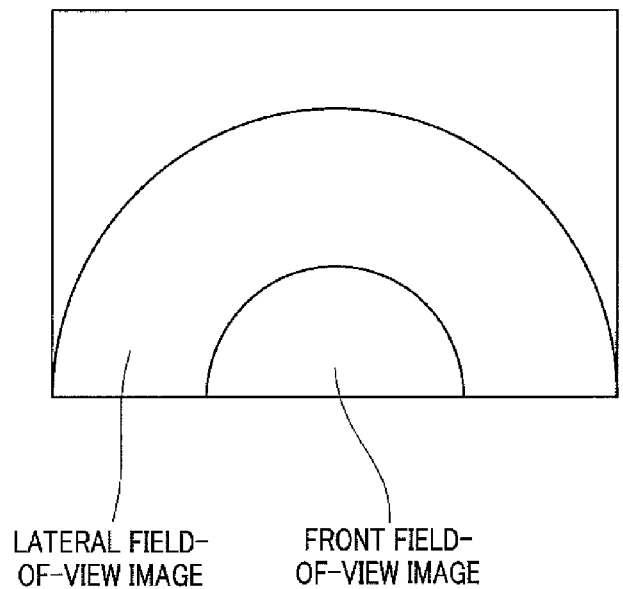
FIG. 8 is a diagram showing an example of a display appearance of an image after transition, which is different from the example of FIG. 7, in the modified example of the first embodiment.

According to the above second processing, when it is detected that the bending portion 7 is bent upward, for example, the image processing section 32a extracts and magnifies an upper half of the observation image shown in FIG. 4. Thereby, the observation image displayed on the monitor 35 is transited from the image shown in FIG. 4 to the image shown in FIG. 8.

Besides, the above second processing is applicable to not only the case where the bending portion 7 is bent upward but also to a case where the bending portion 7 is bent in a direction other than the upward direction in substantially the same manner.

As described above, according to the modified examples of the present embodiment, in an observation image allowing the observation in the front-viewing direction and also in the lateral-viewing direction simultaneously, the display appearance of the observation image can be transited appropriately in accordance with the bending direction of the bending portion, and therefore visibility in the bending operation can be improved.

Second Embodiment

Next, a second embodiment of the present invention will be described.

It is noted that a detailed description regarding a part having the same configuration as the first embodiment will be omitted. Further, an endoscope system of this embodiment follows the external appearance as shown in FIG. 1 through FIG. 3 and the display appearance as shown in FIG. 4, but comprises components a part of which is different from the configuration of the main part as shown in FIG. 5. Therefore, the part different from the configuration of the main part as shown in FIG. 5 will be mainly described.

Figure 9:
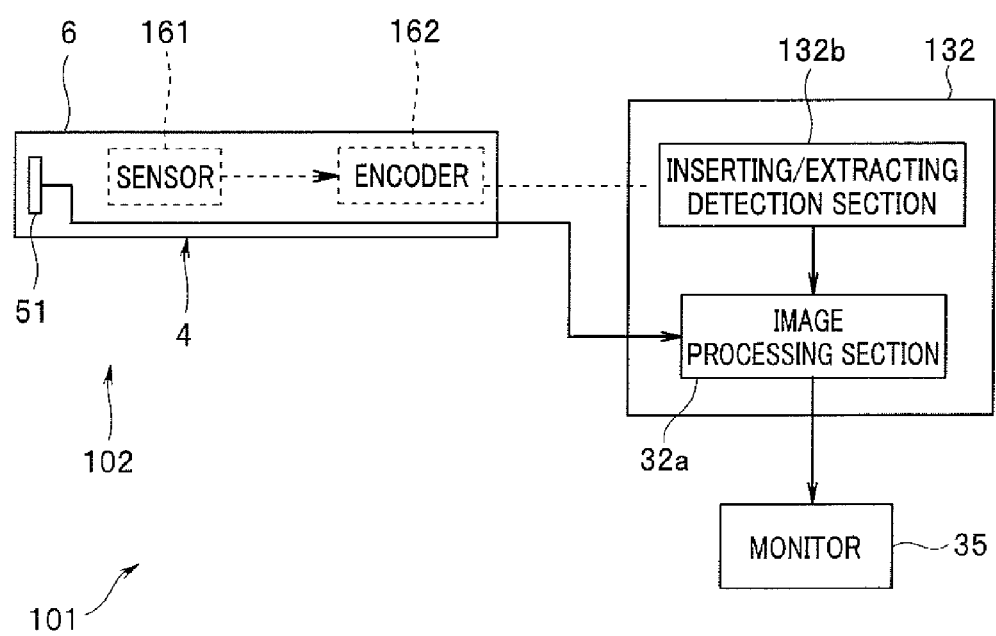
FIG. 9 is a diagram showing a configuration of a main part in a second embodiment.

First, in an endoscope system 101, the main part of which is shown in FIG. 9, respective components of the image pickup device 51 provided at the distal end portion 6 of the endoscope 102, the light source apparatus 31, the video processor 132 and the monitor 35 are started up and thereby an image pickup signal is outputted from the image pickup device 51.

The image processing section 32a of the video processor 132 generates a video signal by performing signal processing with respect to an image pickup signal outputted from the image pickup device 51 and outputs the video signal to the monitor 35. Thereby, an observation image as shown in FIG. 4 is displayed on the monitor 35.

On the other hand, the operator moves the distal end portion 6 close to a desired location in a body cavity by appropriately inserting or extracting the insertion portion 4 of the endoscope in the body cavity.

At the distal end portion 6 of the endoscope 102 or in the vicinity thereof, there is provided a sensor 161 (see FIG. 9) capable of detecting information about a moving direction of the insertion portion 4 as a physical amount and outputting a signal containing the information. Specifically, the sensor 161 is configured by an acceleration sensor capable of detecting and outputting a temporal displacement of position of the insertion portion 4 as acceleration, or an optical sensor capable of detecting and outputting a displacement amount (motion amount) of position of the insertion portion 4 per unit time, and the like.

In addition, an encoder 162 (see FIG. 9) capable of converting the information detected by the sensor 161 into an electric signal and outputting the signal to the video processor 132 is provided in a subsequent step of the sensor 161 of the insertion portion 4 of the endoscope 102.

An inserting/extracting detection section 132b (see FIG. 9) of the video processor 132 detects whether the moving direction of the insertion portion 4 is forward (in an inserting direction) or backward (in an extracting direction) based on the electric signal outputted from the encoder 162 and outputs a detection result to the image processing section 32a.

When a detection result that the insertion portion 4 is moving forward (in inserting direction) is outputted from the inserting/extracting detection section 132b, the image processing section 32a performs processing of magnifying the front field-of-view image (enlarging the display size on the monitor 35) and changing the display appearance of the lateral field-of-view image in accordance with the magnification of the front field-of-view image.

Specifically, the image processing of changing the display appearance of the lateral field-of-view image may be, for example, processing of displaying only a part (a central side of the original image) of the original lateral field-of-view image in a range adjacent to the magnified front field-of-view image on the monitor 35, and processing of displaying only a part (an outer peripheral side of the original image) of the original lateral field-of-view image in a range not covered by the magnified front field-of-view image on the monitor 35. Alternatively, the image processing of changing the display appearance of the lateral field-of-view image may be, for example, processing of displaying a compressed image obtained by performing image compression processing with respect to the original lateral field-of-view image while maintaining the field-of-view range of the original lateral field-of-view image on the monitor 35.

Then, the image processing section 32a generates an observation image in a display appearance as shown in FIG. 13, for example, by performing the above-mentioned processing with respect to the front field-of-view image and the lateral field-of-view image, and outputs the observation image to the monitor 35. In the observation image exemplified in FIG. 13, an image which corresponds to a part of the original lateral field-of-view image or a compressed image of the original lateral field-of-view image is displayed with the magnified display of the front field-of-view image.

Here, in the inserting operation of the insertion portion, it is highly possible that a situation arises that requires attention to be paid mainly in the front-viewing direction. Then, according to the observation image having the display appearance as shown in FIG. 13, the operator can smoothly perform the inserting operation of the insertion portion 4 while viewing the magnified front field-of-view image.

Further, when a detection result that the insertion portion 4 is moving backward (in the extracting direction) is outputted from the inserting/extracting detection section 132b, the image processing section 32a performs processing of magnifying the lateral field-of-view image (enlarging the display size on the monitor 35) and changing the display appearance of the front field-of-view image in accordance with the magnification of the lateral field-of-view image.

Specifically, the image processing of changing the display appearance of the front field-of-view image may be, for example, processing of displaying only a part (an outer peripheral side of the original image) of the original front field-of-view image in a range adjacent to the magnified lateral field-of-view image on the monitor 35, and processing of displaying only a part (a central side of the original image) in a range not covered by the magnified lateral field-of-view image on the monitor 35. Alternatively, the image processing of changing the display appearance of the front field-of-view image may be, for example, processing of displaying a compressed image obtained by performing image compression processing with respect to the original front field-of-view image while maintaining the field-of-view range of the original front field-of-view image on the monitor 35.

Figure 14:
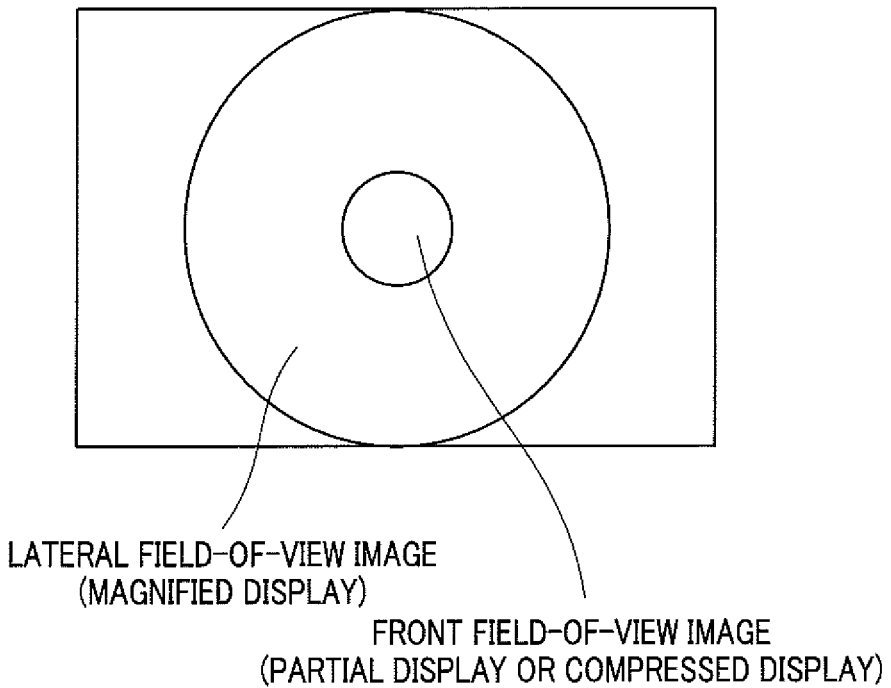
FIG. 14 is a diagram showing an example of a display appearance of the observation image of FIG. 4 in which a lateral field-of-view image is magnified.

Then, the image processing section 32a generates an observation image in a display appearance as shown in FIG. 14, for example, by performing the above-mentioned processing with respect to the front field-of-view image and the lateral field-of-view image, and outputs the observation image to the monitor 35. In the observation image exemplified in FIG. 14, an image which corresponds to a part of the original front field-of-view image or a compressed image of the original front field-of-view image is displayed with the magnified display of the lateral field-of-view image.

In addition, the image processing section 32a of the present embodiment may generate an observation image which has the display appearance as shown in FIG. 14 and the entire field-of-view angle of 230° including a rear field-of-view angle of 50° with respect to an insertion axis direction of the insertion portion 4.

Here, in the extracting operation of the insertion portion, it is highly possible that a situation arises that requires attention to be paid mainly in the lateral-viewing direction. Then, according to the observation image having the display appearance as shown in FIG. 14, the operator can smoothly perform the extracting operation of the insertion portion 4 while viewing the magnified lateral field-of-view image.

In addition, according to the present embodiment, instead of the endoscope system 101 shown in FIG. 9 which is configured to include the sensor 161 and the encoder 162, the embodiment may be configured as an endoscope system 101A shown in FIG. 10 which acquires information about the moving direction of the insertion portion 4 of the endoscope 2 using an insertion shape acquiring apparatus 163.

Specifically, the insertion shape acquiring apparatus 163 of the endoscope system 101A, the main part of which is shown in FIG. 10, is configured as an X-ray image pickup apparatus capable of acquiring an X-ray image of the insertion portion 4 and outputting a signal to the inserting/extracting detection section 132b. In this case, the inserting/extracting detection section 132b detects whether the moving direction of the insertion portion 4 is forward (insertion direction) or backward (extracting direction) by comparing two adjacent X-ray images in time series among the X-ray images successively outputted from the insertion shape acquiring apparatus 163, and outputs a detection result to the image processing section 32a.

Alternatively, the insertion shape acquiring apparatus 163 is configured, for example, as an endoscope insertion shape detection apparatus which is capable of detecting, by a magnetic field detecting section (not shown), a magnetic field generated by driving of a plurality of magnetic field generation devices (not shown) arranged in the insertion portion 4, generating an insertion shape image of the insertion portion 4 according to the magnetic field and outputting a signal to the inserting/extracting detection section 132b. In this case, the inserting/extracting detection section 132b detects whether the moving direction of the insertion portion 4 is forward (insertion direction) or backward (extracting direction) by comparing two adjacent insertion shape images in time series among the insertion shape images successively outputted from the insertion shape acquiring apparatus 163, and outputs a detection result to the image processing section 32a.

As described above, according to the present embodiment, in the observation image allowing the observation in the front-viewing direction and also in the lateral-viewing direction simultaneously, visibility of the image in one of the viewing directions can be improved in accordance with the inserting operation and the extracting operation of the insertion portion of the endoscope.

Third Embodiment

Next, a third embodiment of the present invention will be described.

It is noted that a detailed description regarding a part having the same configuration as the first embodiment or the second embodiment will be omitted. Further, an endoscope system of this embodiment follows the external appearance as shown in FIG. 1 through FIG. 3 and the display appearance as shown in FIG. 4, but comprises components a part of which is different from the configuration of the main part as shown in FIG. 5. Therefore, the part different from the configuration of the main part as shown in FIG. 5 will be mainly described.

First, in an endoscope system 201, the main part of which is shown in FIG. 11, respective components of the image pickup device 51 provided at the distal end portion 6 of the endoscope 2, the light source apparatus 31, the video processor 232 and the monitor 35 are started up and thereby an image pickup signal is outputted from the image pickup device 51.

The image processing section 32a of the video processor 232 generates a video signal by performing signal processing with respect to an image pickup signal outputted from the image pickup device 51 and outputs the video signal to an image analyzing section 232b (see FIG. 11) and the monitor 35. Thereby, an observation image as shown in FIG. 4 is displayed on the monitor 35.

The image analyzing section 232b of the video processor 232 is set in advance such that an object having a predetermined color or a predetermined brightness is designated as a landmark in the observation image according to the video signal outputted from the image processing section 32a.

Further, the image analyzing section 232b detects whether the aforesaid landmark is moving toward a peripheral side of the observation image or toward a central side of the observation image by comparing two adjacent frames of the observation image in time series, and outputs a detection result to the image processing section 32a. Specifically, the image analyzing section 232b detects the moving direction of the aforesaid landmark by performing calculation using a spatial gradient or a temporal gradient (optical flow) of the brightness in the observation image, and outputs a detection result to the image processing section 32a.

When a detection result that the aforesaid landmark is moving toward the peripheral side of the observation image is outputted from the image analyzing section 232b, (since it is assumed that the insertion portion 4 is being inserted) the image processing section 32a performs processing of magnifying the front field-of-view image (enlarging the display size on the monitor 35) and image processing of changing the display appearance of the lateral field-of-view image in accordance with the magnification of the front field-of-view image.

Specifically, the image processing of changing the display appearance of the lateral field-of-view image may be, for example, processing of displaying only a part (a central side of the original image) of the original lateral field-of-view image in a range adjacent to the magnified front field-of-view image on the monitor 35, and processing of displaying only a part (an outer peripheral side of the original image) of the original lateral field-of-view image in a range not covered by the magnified front field-of-view image on the monitor 35. Alternatively, the image processing of changing the display appearance of the lateral field-of-view image may be, for example, processing of displaying a compressed image obtained by performing image compression processing with respect to the original lateral field-of-view image while maintaining the field-of-view range of the original lateral field-of-view image on the monitor 35.

Then, the image processing section 32a generates an observation image in a display appearance as shown in FIG. 13, for example, by performing the above-mentioned processing with respect to the front field-of-view image and the lateral field-of-view image, and outputs the observation image to the monitor 35. In the observation image exemplified in FIG. 13, an image which corresponds to a part of the original lateral field-of-view image or a compressed image of the original lateral field-of-view image is displayed with the magnified display of the front field-of-view image.

Here, in the inserting operation of the insertion portion, it is highly possible that a situation arises that requires attention to be paid mainly in the front-viewing direction. Then, according to the observation image having the display appearance as shown in FIG. 13, the operator can smoothly perform the inserting operation of the insertion portion 4 while viewing the magnified front field-of-view image.

Further, when a detection result that the aforesaid landmark is moving toward the central side of the observation image is outputted from the image analyzing section 232b, (since it is assumed that the insertion portion 4 is being extracted) the image processing section 32a performs processing of magnifying the lateral field-of-view image (enlarging the display size on the monitor 35) and image processing of changing the display appearance of the front field-of-view image in accordance with the magnification of the lateral field-of-view image.

Specifically, the image processing of changing the display appearance of the front field-of-view image may be, for example, processing of displaying only a part (an outer peripheral side of the original image) of the original front field-of-view image in a range adjacent to the magnified lateral field-of-view image on the monitor 35, and processing of displaying only a part (a central side of the original image) in a range not covered by the magnified lateral field-of-view image on the monitor 35. Alternatively, the image processing of changing the display appearance of the front field-of-view image may be, for example, processing of displaying a compressed image obtained by performing image compression processing with respect to the original front field-of-view image while maintaining the field-of-view range of the original front field-of-view image on the monitor 35.

Then, the image processing section 32a generates an observation image in a display appearance as shown in FIG. 14, for example, by performing the above-mentioned processing with respect to the front field-of-view image and the lateral field-of-view image, and outputs the observation image to the monitor 35. In the observation image exemplified in FIG. 14, an image which corresponds to a part of the original front field-of-view image or a compressed image of the original front field-of-view image is displayed with the magnified display of the lateral field-of-view image.

In addition, the image processing section 32a of the present embodiment may generate an observation image which has the display appearance as shown in FIG. 14 and the entire field-of-view angle of 230° including a rear field-of-view angle of 50° with respect to an insertion axis direction of the insertion portion 4.

Here, in the extracting operation of the insertion portion, it is highly possible that a situation arises that requires attention to be paid mainly in the lateral-viewing direction. Then, according to the observation image having the display appearance as shown in FIG. 14, the operator can smoothly perform the extracting operation of the insertion portion 4 while viewing the magnified lateral field-of-view image.

Besides, the image analyzing section 232b may output a detection result that the aforesaid landmark is not moving, in addition to the detection result that the aforesaid landmark is moving toward the peripheral side or the central side of the observation image. In accordance with this, when the image processing section 32a receives a detection result that the aforesaid landmark is not moving from the image analyzing section 232b, (since it is assumed that the insertion portion 4 is not moving) the image processing section 32a may maintain the display appearance of the observation image to be the same as the previous one.

Further, the image analyzing section 232b of the present embodiment is not limited to a configuration of detecting whether the aforesaid landmark is moving toward the peripheral side or the central side of the observation image, but may have a configuration of detecting a temporal change of a size of the aforesaid landmark in the observation image based on comparison of two adjacent frames of the observation image in time series. In accordance with this, when the image processing section 32a receives a detection result that the size of the aforesaid landmark is gradually increased, the image processing section 32a generates the observation image as exemplified in FIG. 13, and when the image processing section 32a receives a detection result that the size of the aforesaid landmark is gradually decreased, the image processing section 32a generates the observation image as exemplified in FIG. 14, and further when the image processing section 32a receives a detection result that the size of the aforesaid landmark is not changed from the image analyzing section 232b, (since it is assumed that the insertion portion 4 is not moving) the image processing section 32a maintains the display appearance of the observation image to be the same as the previous one.

Figure 19:
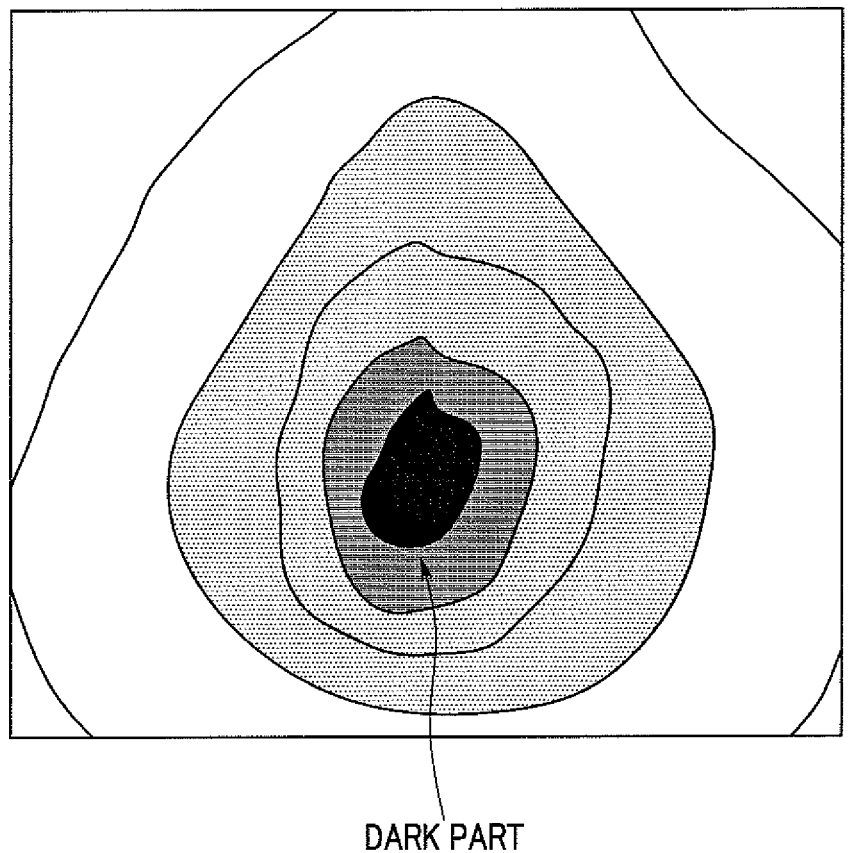
FIG. 19 is a diagram showing an example of an image including a dark part in a lumen.

Furthermore, as shown in FIG. 19, for example, when observing the interior of a lumen, since the illumination light is hard to reach a deeper side in an advancing direction of the insertion portion inserted into the lumen (a deep portion in the opening direction), the deeper side is displayed as a dark part. The image analyzing section 232b of this embodiment utilize this and may be the one that detects whether the dark part (in the advancing direction of the insertion portion 4 inserted into the lumen) is positioned in the front field-of-view image of the present observation image or in the lateral field-of-view image of the present observation image. In accordance with this, when the image processing section 32a receives a detection result that the dark portion is present in the front field-of-view image from the image analyzing section 232b, the image processing section 32a may generate the observation image as exemplified in FIG. 13, and when the image processing section 32a receives a detection result that the dark portion is present in the lateral field-of-view image from the image analyzing section 232b, the image processing section 32a may generate the observation image as exemplified in FIG. 14.

As described above, according to the present embodiment, in the observation image allowing the observation in the front-viewing direction and also in the lateral-viewing direction simultaneously, visibility of the image in one of the viewing directions can be improved in accordance with the present observation situation of the endoscope.

Fourth Embodiment

Next, a fourth embodiment of the present invention will be described.

It is noted that a detailed description regarding a part having the same configuration as the first embodiment, the second embodiment or the third embodiment will be omitted. Further, an endoscope system of this embodiment follows the external appearance as shown in FIG. 1 through FIG. 3 and the display appearance as shown in FIG. 4, but comprises components a part of which is different from the configuration of the main part as shown in FIG. 5. Therefore, the part different from the configuration of the main part as shown in FIG. 5 will be mainly described.

Figure 12:
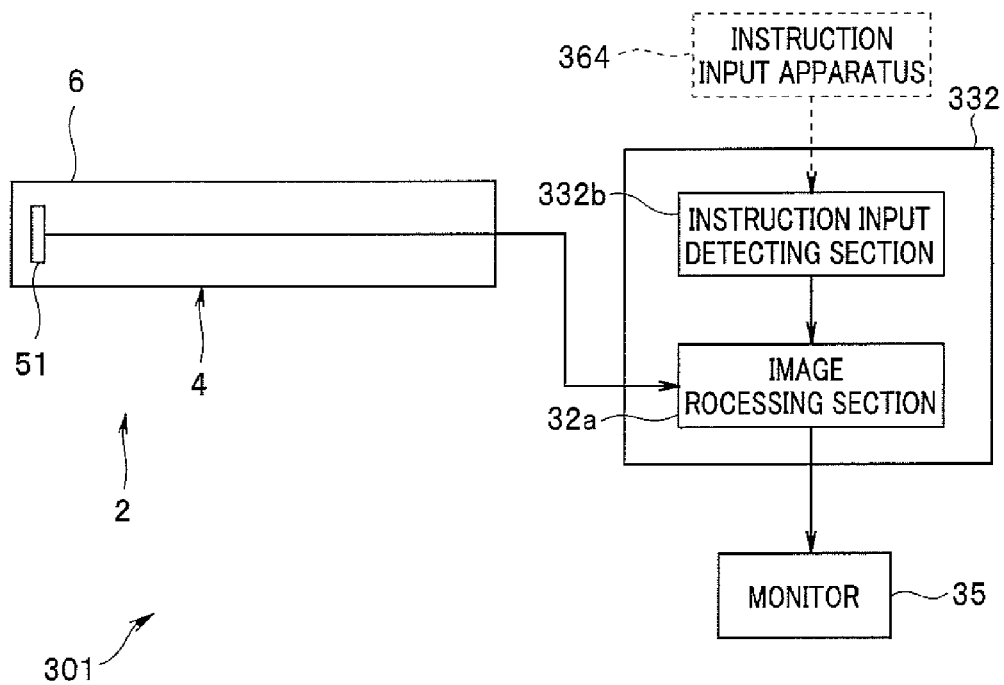
FIG. 12 is a diagram showing a configuration of a main part in a fourth embodiment.

First, in an endoscope system 301, the main part of which is shown in FIG. 12, respective components of the image pickup device 51 provided at the distal end portion 6 of the endoscope 2, the light source apparatus 31, the video processor 332 and the monitor 35 are started up and thereby an image pickup signal is outputted from the image pickup device 51.

The image processing section 32a of the video processor 332 generates a video signal by performing signal processing with respect to an image pickup signal outputted from the image pickup device 51 and outputs the video signal to the monitor 35. Thereby, an observation image as shown in FIG. 4 is displayed on the monitor 35.

The operator gives an instruction to magnify one of the front field-of-view image and the lateral field-of-view image in the observation image displayed on the monitor 35 by an input operation on an instruction input apparatus 364. Besides, the instruction input apparatus 364 may be configured as a single apparatus or may be incorporated in any of the apparatuses which the endoscope system 301 is provided with. Specifically, the instruction input apparatus 364 may be any of the scope switches 25, the keyboard 34, an operation panel of the video processor 332 and a foot switch.

An instruction input detecting section 332b of the video processor 332 detects whether the instruction given on the instruction input apparatus 364 is an instruction to magnify the front field-of-view image or an instruction to magnify the lateral field-of-view image, and outputs a detection result to the image processing section 32a.

When a detection result that an instruction is given to magnify the front field-of-view image is outputted from the instruction input detecting section 332b, the image processing section 32a performs processing of magnifying the front field-of-view image (enlarging the display size on the monitor 35) and changing the display appearance of the lateral field-of-view image in accordance with the magnification of the front field-of-view image.

Specifically, the image processing of changing the display appearance of the lateral field-of-view image may be, for example, processing of displaying only a part (a central side of the original image) of the original lateral field-of-view image in a range adjacent to the magnified front field-of-view image on the monitor 35, and processing of displaying only a part (an outer peripheral side of the original image) of the original lateral field-of-view image in a range not covered by the magnified front field-of-view image on the monitor 35. Alternatively, the image processing of changing the display appearance of the lateral field-of-view image may be, for example, processing of displaying a compressed image obtained by performing image compression processing with respect to the original lateral field-of-view image while maintaining the field-of-view range of the original lateral field-of-view image on the monitor 35.

Then, the image processing section 32a generates an observation image in a display appearance as shown in FIG. 13, for example, by performing the above-mentioned processing with respect to the front field-of-view image and the lateral field-of-view image, and outputs the observation image to the monitor 35. In the observation image exemplified in FIG. 13, an image which corresponds to a part of the original lateral field-of-view image or a compressed image of the original lateral field-of-view image is displayed with the magnified display of the front field-of-view image.

Further, when a detection result that an instruction is given to magnify the lateral field-of-view image is outputted from the instruction input detecting section 332b, the image processing section 32a performs processing of magnifying the lateral field-of-view image (enlarging the display size on the monitor 35) and changing the display appearance of the front field-of-view image in accordance with the magnification of the lateral field-of-view image.

Specifically, the image processing of changing the display appearance of the front field-of-view image may be, for example, processing of displaying only a part (an outer peripheral side of the original image) of the original front field-of-view image in a range adjacent to the magnified lateral field-of-view image on the monitor 35, and processing of displaying only a part (a central side of the original image) in a range not covered by the magnified lateral field-of-view image on the monitor 35. Alternatively, the image processing of changing the display appearance of the front field-of-view image may be, for example, processing of displaying a compressed image obtained by performing image compression processing with respect to the original front field-of-view image while maintaining the field-of-view range of the original front field-of-view image on the monitor 35.

Then, the image processing section 32a generates the observation image in a display appearance as shown in FIG. 14, for example, by performing the above-mentioned processing with respect to the front field-of-view image and the lateral field-of-view image, and outputs the observation image to the monitor 35. In the observation image exemplified in FIG. 14, an image which corresponds to a part of the original front field-of-view image or a compressed image of the original front field-of-view image is displayed with the magnified display of the lateral field-of-view image.

In addition, the image processing section 32a of the present embodiment may generate an observation image which has the display appearance as shown in FIG. 14 and the entire field-of-view angle of 230° including a rear field-of-view angle of 50° with respect to an insertion axis direction of the insertion portion 4.

It is noted that the instruction input apparatus 364 is not limited to being configured by the above-mentioned apparatuses, and may be configured by a microphone capable of capturing a voice of the operator as an audio signal. In accordance with this, the instruction input detecting section 332b may be the one which detects whether an instruction to magnify the front field-of-view image or an instruction to magnify the lateral field-of-view image is given by performing a voice analysis on the audio signal outputted from the instruction input apparatus 364.

Further, in this embodiment, in addition to the instruction to magnify the front field-of-view image and the instruction to magnify the lateral field-of-view image, the instruction input apparatus 364 may be configured such that an instruction may be given for returning the display appearance of the observation image to the display appearance as shown in FIG. 4.

As described above, according to the present embodiment, in the observation image allowing the observation in the front-viewing direction and also in the lateral-viewing direction simultaneously, a display appearance can be obtained such that visibility of the image in desired one of the field-of-view directions is improved. Further, the switching control of the display appearance by the input operation on the instruction input apparatus 364 of the present embodiment may be combined with the automatic display appearance switching control as described in the first to third embodiments. In such case, by setting the switching by the input operation on the instruction input apparatus 364 to be prior to the automatic switching control, for example, a desired display appearance according to the operator's intention can be selected.

Besides, the present invention is not limited to the above-described embodiments and it is a matter of course that various modifications and applications are possible within a scope not departing from the gist of the invention.

What is claimed is:

1. An endoscope system comprising:
   an endoscope which has an insertion portion and acquires a front field-of-view image and a lateral field-of-view image of an object of observation;
   a detecting section which has a function capable of detecting whether a treatment instrument is used or not in the endoscope based on a notification signal which is outputted when the treatment instrument is inserted into the endoscope or a function capable of detecting a moving direction of the insertion portion based on an acceleration or a change of a motion amount as information about the moving direction of the insertion portion; and
   an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section,
   wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

2. An endoscope system comprising:
an endoscope which has an insertion portion and acquires a front field-of-view image and a lateral field-of-view image of an object of observation;
an insertion shape acquiring apparatus for acquiring an insertion shape of the insertion portion provided in the endoscope;
a detecting section which has a function capable of detecting whether a treatment instrument is used or not in the endoscope based on a notification signal which is outputted when the treatment instrument is inserted into the endoscope or a function capable of detecting a moving direction of the insertion portion based on a signal indicative of the insertion shape of the insertion portion obtained by the insertion shape acquiring apparatus; and
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section,
wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

3. An endoscope comprising:
an endoscope which has an insertion portion and one or more switches for outputting signals for instructing a start of a forward water feed and which acquires a front field-of-view image and a lateral field-of-view image of an object of observation;
a detecting section which has a function capable of detecting that one function corresponding to the signal outputted from switches is turned on or off based on the signal outputted from the switches or a function capable of detecting a moving direction of the insertion portion based on an acceleration or a change of a motion amount as information about the moving direction of the insertion portion; and
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section,
wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of view angle of 230° including a rear field-of-view angle of 50° with respect to an insertion axis direction of the insertion portion.

4. An endoscope system comprising:
an endoscope which has an insertion portion and one or more switches for outputting signals for instructing a start of a forward water feed and which acquires a front field-of-view image and a lateral filed-of-view image of an object of observation;
an insertion shape acquiring apparatus for acquiring an insertion shape of the insertion portion provided in the endoscope;
a detecting section which has a function capable of detecting that one function corresponding to the signal outputted from the switches is turned on or off based on the signal outputted from the switches or a function capable of detecting a moving direction of the insertion portion based on an acceleration or a change of a motion amount as information about the moving direction of the insertion portion; and
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section,
wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a real' field-of-view angle of 50° with respect to an insertion axis direction of the insertion portion.

5. An endoscope system comprising:
an endoscope which has an insertion portion and acquires a front field-of-view image and a lateral field-of-view image of an object of observation;
a detecting section which has a function capable of detecting information about a predetermined landmark included in at least one of the front field-of-view image and a lateral field-of-view image, or a function capable of detecting a moving direction of the insertion portion based on an acceleration or a change of a motion amount as information about the moving direction of the insertion portion; and
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section;
wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

6. The endoscope system according to claim 5, wherein the detecting section detects the moving direction of the predetermined landmark as the information about the predetermined landmark.

7. The endoscope system according to claim 5, wherein the detecting section detects a temporal change of a size of the predetermined landmark as the information about the predetermined landmark.

8. The endoscope system according to claim 5, wherein the detecting section detects a position of a predetermined landmark as the information about the predetermined landmark.

9. An endoscope system comprising:
an endoscope which has an insertion portion and acquires a front field-of-view image and a lateral field-of-view image of an object of observation;
an insertion shape acquiring apparatus for acquiring an insertion shape of the insertion portion provided in the endoscope;
a detecting section which has a function capable of detecting information about a predetermined landmark included in the observation image, or a function capable of detecting a moving direction of the insertion portion based on a signal indicative of the insertion shape of the insertion portion obtained by the insertion shape acquiring apparatus; and
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field of-view image on the display section,
wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

10. The endoscope system according to claim 9, wherein the detecting section detects the moving direction of the predetermined landmark as the information about the predetermined landmark.

11. The endoscope system according to claim 9, wherein the detecting section detects a temporal change of a size of the predetermined landmark as the information about the predetermined landmark.

12. The endoscope system according to claim 9, wherein the detecting section detects a position of the predetermined landmark as the information about the predetermined landmark.

13. An endoscope system comprising:
an endoscope which has an insertion portion and acquires a front field-of-view image and a lateral field-of-view image of an object of observation;
an instruction input apparatus capable of performing at least two instructions of an instruction for magnifying the front field-of-view image and an instruction for magnifying the lateral field-of-view image;
a detecting section which has a function capable of detecting which one of the two instructions is made in the instruction input apparatus or a function capable of detecting a moving direction of the insertion portion based on an acceleration or a change of a motion amount as information about the moving direction of the insertion portion;
an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compress processing of displaying a compressed image of the front field-of-view image on the display section, wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

14. An endoscope system comprising:

an endoscope which has an insertion portion and acquires a front filed-of-view image and a lateral field-of-view image of an object of observation;

an instruction input apparatus capable of performing at least two instructions of an instruction for magnifying the front field-of-view image and an instruction for magnifying the lateral field-of-view image;

an insertion shape acquiring apparatus for acquiring an insertion shape of the insertion portion provided in the endoscope;

a detecting section which has a function capable of detecting which one of the two instructions is made in the instruction input apparatus or a function capable of detecting a moving direction of the insertion portion based on a signal indicative of the insertion shape of the insertion portion obtained by the insertion shape acquiring apparatus; and an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section, wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

15. An endoscope system comprising:

an endoscope which has an insertion portion, a bending portion and a bending operation lever capable of making a bending action of the bending portion, and which acquires a front field-of-view image and a lateral field-of-view image of an object of observation;

a detecting section which has a function capable of detecting a bending direction of the bending portion based on an operation state of the bending operation lever or a function capable of detecting a moving direction of the insertion portion based on an acceleration or a change of a motion amount as information about the moving direction of the insertion portion; and an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumference of the front field-of-view image, or a compressed image of the lateral field-of-view image, and performs in a case where the one field-of-view image is the lateral field-of-view image, image compression processing of displaying a compressed image of the front field-of-view image on the display section, wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

16. An endoscope system comprising:

an endoscope which has an insertion portion, a bending portion and a bending operation lever capable of making a bending action of the bending portion, and which acquires a front field-of-view image and a lateral field-of-view image of an object of observation;

an insertion shape acquiring apparatus for acquiring an insertion shape of the insertion portion provided in the endoscope;

a detecting section which has a function capable of detecting a bending direction of the bending portion based on an operation state of the bending operation lever or a function capable of detecting a moving direction of the insertion portion based on a signal indicative of the insertion shape of the insertion portion obtained by the insertion shape acquiring apparatus; and an image processing section which generates a lateral field-of-view image having a circular ring shape to be adjacent to an outer circumference of the front field-of-view image having a round shape as an observation image in the same screen, displays a magnified image of one field-of-view image out of the front field-of-view image and the lateral field-of-view image on a display section based on a detection result of the detecting section, displays, in a case where the one field-of-view image is the front field-of-view image, only a part of the lateral field-of-view image on an insertion direction side of the endoscope which is a part adjacent to the outer circumferential of the front field-of-view image, or a compressed image of the lateral field-of-view image, and performs in a case where the one field-of-view image is the lateral field-of-view image, image compression processing of displaying a compressed image of the front field-of-view image on the display section, wherein when the detection result that the moving direction of the endoscope is an extracting direction is obtained by the detecting section, the image processing section performs processing for displaying a magnified image of the lateral field-of-view image on the display section, and instead of the adjacent part display processing and the image compression processing, generates an observation image having an entire field-of-view angle of 230° including a rear field-of-view angle of 50° with respect to an insertion axis direction of the insertion portion.

\* \* \* \* \*